United States Patent [19]

Lenselink

[11] 4,456,561
[45] Jun. 26, 1984

[54] NITRILES AND USE AS PERFUME CHEMICALS

[75] Inventor: Willem Lenselink, Voorthuizen, Netherlands

[73] Assignee: Polak's Frutal Works, B.V., Amersfoort, Netherlands

[21] Appl. No.: 351,088

[22] Filed: Feb. 22, 1982

Related U.S. Application Data

[62] Division of Ser. No. 123,581, Feb. 22, 1980, Pat. No. 4,336,204, which is a division of Ser. No. 20,308, Mar. 14, 1979, Pat. No. 4,235,805.

[30] Foreign Application Priority Data

Mar. 20, 1978 [GB] United Kingdom ............... 10938/78

[51] Int. Cl.³ .......................................... C07C 121/46
[52] U.S. Cl. .................................. 260/464; 252/522 R
[58] Field of Search .................. 260/464, 465–469; 252/522

[56] References Cited

U.S. PATENT DOCUMENTS

| | | | |
|---|---|---|---|
| 3,168,550 | 2/1965 | Blumenthal | 260/464 |
| 3,531,510 | 9/1970 | Blumenthal | 260/465.9 |
| 3,655,722 | 4/1972 | Mitchell et al. | 260/465.9 |
| 3,869,493 | 3/1975 | Bozzato et al. | 252/522 R |
| 4,132,677 | 1/1979 | Shaffer et al. | 252/522 R |
| 4,156,690 | 5/1979 | De Simone | 252/522 R X |
| 4,193,934 | 3/1980 | Bauer et al. | 260/464 X |

FOREIGN PATENT DOCUMENTS 2656065 6/1977 Fed. Rep. of Germany .

*Primary Examiner*—Joseph Paul Brust

[57] ABSTRACT

Novel nitriles based on the carbon skeleton of menthane are disclosed, having the structural formula

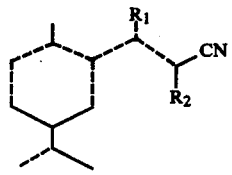

These compounds are useful in a variety of perfumery applications.

1 Claim, No Drawings

NITRILES AND USE AS PERFUME CHEMICALS

This is a division of application Ser. No. 123,581, filed Feb. 22, 1980, now U.S. Pat. No. 4,336,204, which is a division of application Ser. No. 020,308 filed Mar. 14, 1979, now U.S. Pat. No. 4,235,805.

This invention relates to new and useful chemical compounds, useful as a perfume or as a component of perfumes. Specifically it relates to nitriles based on the skeleton of 1-methyl-4-isopropylcyclohexane. In recent years a trend in perfumery is observable in the direction of the use of nitriles, which class of compounds has previously been rather unexploited for perfumery purposes.

Besides the desirable olfactory properties of the nitriles for modern perfumery, most of the nitriles which have to date found acceptance in perfumery also possess desirable properties with respect to chemical stability and resistance to discolouration in many applications, e.g. in soap and other cosmetic preparations, where many otherwise useful perfumery chemicals are not stable. In particular 3,7-dimethyl-6-octenenitrile, 3,7-dimethyl-2,6-octadienenitrile and also 3-phenylacrylonitrile are useful in perfumery.

It is the object of present invention to provide a novel class of nitriles based on the carbon skeleton of 1-methyl-4-isopropylcyclohexane. These novel nitriles are represented by formula I, wherein $R_1$ and $R_2$ represent hydrogen or an alkyl group of about 1 to 6 carbon atoms and the total carbon number of $R_1$ and $R_2$ is 6 or less and wherein the dotted lines represent C—C double or single bonds with the limitation that no more than one such double bond can be present in the six-membered ring and no more than one in the nitrile group containing side chain. It will be understood that the double bonds, when present, must be so located as to satisfy the tetravalent carbon concept.

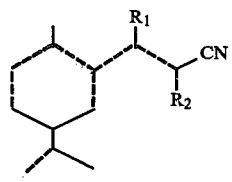
I

Examplary, but by no means all, compounds of the invention having the specified structure are:
3-(1-methyl-4-isopropylcyclohexyl-2)acrylonitrile
3-(1-methyl-4-isopropylcyclohexylidene-2)propanenitrile
2-n-hexyl-3-(1-methyl-4-isopropylcyclohexylidene-2)propanenitrile
2-methyl-3-(1-methyl-4-isopropylcyclohexenyl-2)-2-butenenitrile
3-(2-methyl-5-isopropylcyclohexenyl-1)-2-butenenitrile
3-(1-methyl-4-isopropenylcyclohexenyl-6)acrylonitrile
3-(3-methyl-6-isopropenylcyclohexenylidene-4)propanenitrile.

It will be apparent that the novel nitriles can exist in a wide variety of stereoisomeric forms and it is intended that these be included within the structural formulae. Whenever a general formula is presented or referred to in the text or in the attached claims, it is intended to include all possible stereoisomeric forms of the compound. The novel nitriles can be prepared by methods known to the art. In a preferred method an oxo-compound of the general formula II wherein

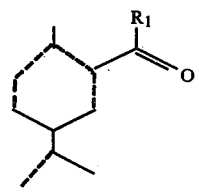
II the dashed lines and $R_1$ are as described above, is reacted with a nitrile group-containing reagent, for example, cyanoacetic acid or its esters, a cyanoalkylphosphonate or an alkylnitrile.

The oxo-compounds represented by formula II can be prepared by methods known to the art. In a preferred method d-,l- or a mixture of the d,l-forms of limonene is converted to p-1-menthene, i.e. 1-methyl-4-isopropylcyclohexene, by partial hydrogenation for example as taught by Y. Kishida, Chem. Pharm. Bull. 8, 357–64 (1960). Hydroformylation of p-1-menthene using a method taught by Falbe, Synthesen mit Kohlenmonoxyde, Springer Verlag, Berlin (1967), pages 3–72, leads to 2-formyl-p-1-menthane. This is a method of preparing compounds wherein $R_1$ is hydrogen.

Another preferred method of preparing the oxo-compound of formula II where $R_1$ is an alkyl radical is by acylation of the p-1-menthene with acid anhydrides or other acid derivatives using the method described in British Pat. No. 870.001. When using this method the oxo compound retains a carbon-to-carbon double bond in the six-membered ring which can subsequently be hydrogenated, if desired.

An indirect method of preparing the oxo-compounds is by way of the Prins reaction of alkenes with aldehydes using the method taught by Roberts in Olah, Friedel-Crafts and Related Reactions, Vol. 3, Interscience Publishers, Inc., New York, 1964, pages 1175–1210, and specifically for p-1-menthene by J. Colonge et al., Bull.Soc.Chim.Fr. 1960, 98. By this method it is also possible to prepare a product which retains a carbon-to-carbon double bond in the six-membered ring. Other methods to prepare the compounds of formula II are by skeletal rearrangements of appropriately substituted β-pinene compounds for example by pyrolysis as taught by Bochwic et al., Bull.Acad.Polon.Ser.-Sci.Chim. 13 (11–12), 751–6 (1965) and by Watanabe, Nippon Kagaku Zasshi 81, 931 (1960), and of appropriately substituted 2-carene compounds by pyrolysis as described by Ohloff, Chem.Ber. 93, 2673 (1960) and in the East German Pat. Nos. 57.850 and 68.903, or by photochemical rearrangement cf. Kropp. J.Am.Chem. Soc. 89, 1126 (1967) and U.S. Pat. No. 3,507,761. These rearrangements lead to oxo-compounds which retain a carbon-to-carbon double bond in the six-membered ring as well as in the isopropyl structure.

The oxo-compounds which contain a carbon-to-carbon double bond in the six-membered ring in the position β,γ to the carbonyl function can be converted to the corresponding compounds with the double bond in the α,β-position by methods known to the art, preferably by alkaline isomerization. In any of the structures, the carbon-carbon double bonds can be partially or fully hydrogenated by conventional hydrogenation methods. The nitriles of this invention are prepared by reacting an oxo-compound of the formula shown above with a reagent containing a nitrile group. One method known for this reaction is the Knoevenagel condensation with cyanoacetic acid or esters thereof—cf. G. Jones in Organic Reactions, John Wiley and Sons, Inc., New York, 1967, volume 15, p. 236–244—followed by decarboxylation.

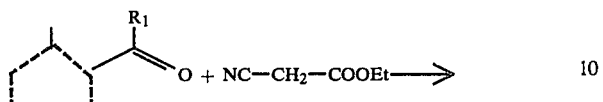

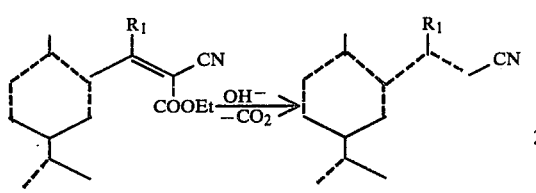

The decarboxylation step can be performed by simple heating of the intermediate alkylidene cyanoacetic acids, but it is preferably carried out in the presence of nitrogen bases such as pyridine, pyrimidine, morpholine, piperidine, triethanolamine, dimethylformamide and the like. Well known decarboxylation catalysts such as copper compounds, for example $Cu_2O$ as taught by Fairhurst, Horwell and Timms, Tetrahedron Letters 1975, p. 3843 can also be used. The alkylidene cyanoacetic ester can be saponified and decarboxylated simultaneously by treating with water in the presence of dimethylformamide or dimethylsulfoxide as described by Krapcho, Jahngen and Lovey, Tetrahedron Letters, 1973, p. 957 and 1974, p. 1091.

Nitriles with saturated nitrogen containing side chains can conveniently be prepared by performing the condensation of the oxo-compound with cyanoacetic esters in a hydrogen atmosphere in the presence of a hydrogenation catalyst as described by Alexander and Cope, J.Am.Chem.Soc. 66, p. 886 (1944).

It will be apparent that the condensation of the oxo-compounds with cyanoacetic acid or ester, followed by decarboxylation leads to nitriles represented by the general formula I in which $R_2$ is hydrogen. It is possible to introduce an alkyl group by direct alkylation of the intermediate alkylidenecyanoacetic ester. This alkylation is preferably carried out in the presence of a strong base such as sodium hydride in an aprotic solvent such as dimethylformamide and an alkylhalide, $R_2X$, wherein X can be chlorine, bromine or iodine. Saponification and decarboxylation of the resulting desubstituted cyanoacetic ester yields nitriles in which $R_2$ is an alkyl radical. The reaction sequence can be represented as follows:

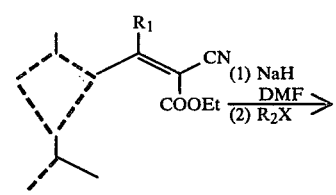

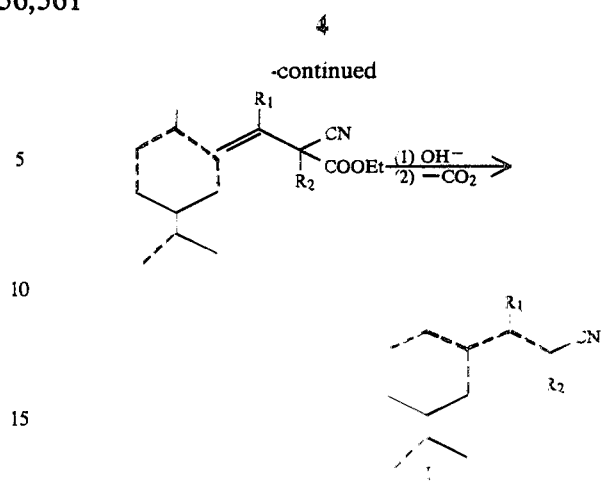

Another preferred method for the preparation of the nitriles of the invention is the Wittig reaction of the oxo-compounds with a cyanoalkylphosphonate in the presence of a base, for example, with $(EtO)_2POCHR_2CN$ as described in the German Pat. No. 1.108.208. Also useful is the two phase modification of this reaction according to Piechucki, Synthesis 1974, p. 869 and to D'Incan and Seyden-Penne, Synthesis 1975, p. 516. The reaction is set forth in the following scheme:

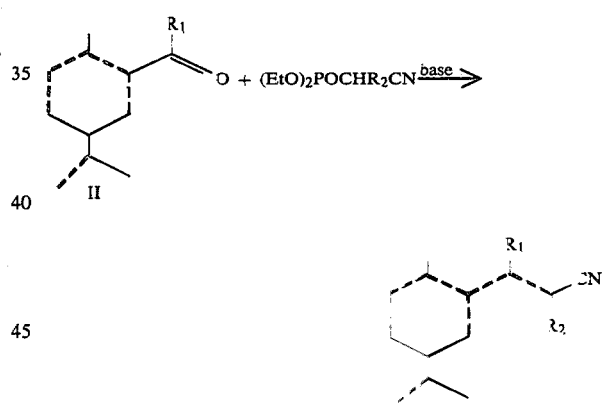

The oxo-compounds can also be condensed directly with alkylnitriles in the presence of an alkaline catalyst such as KOH. However this method is less attractive due to inferior yields in comparison with the other methods. Furthermore, some of the oxo-compounds, especially the aldehyde, are not sufficiently stable under the reaction conditions employed.

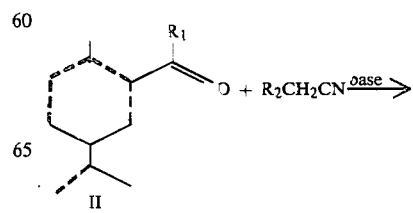

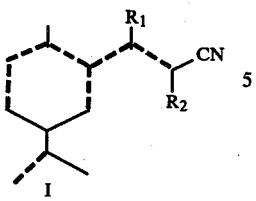

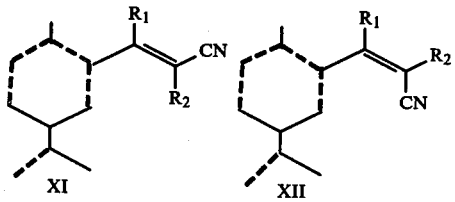

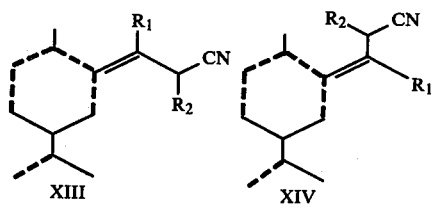

The starting material for preparing the oxo-compounds of formula II can be in a dextrorotatory or levorotatory optical configuration or a mixture of the two. Depending on the configuration of the starting material employed, the nitriles of the invention can exist in a variety of stereoisomeric forms. Since, for example, the starting material, p-1-menthene, exists both in a (+) and a (−) optical configuration the same can be expected in the oxo-compounds II derived from these p-1-menthenes. There is a possibility of eight 2-formyl-p-menthanes derived from a d,l-mixture of p-1-menthenes. These are represented by the following structural formulae:

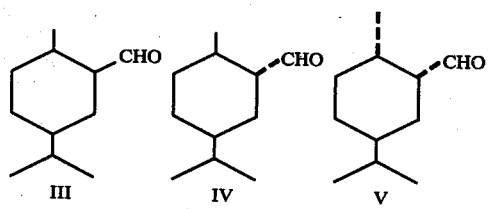

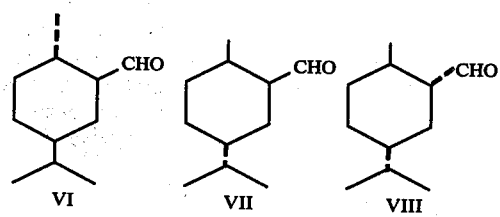

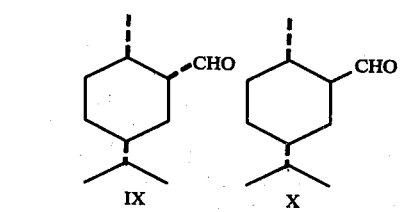

It will also be apparent, as shown by the general formulae, that the nitriles of the invention which possess a double bond in the nitrogen-containing side chain, can exist in two isomeric forms with respect to the position of the double bond relative to the nitrile group. This position can either be $\alpha,\beta$ or $\beta,\gamma$- to the nitrile group. Furthermore in either of these positions, double bonds can exist in an E- or Z-configuration, so that a total of 4 isomeric nitriles, represented by the formulas XI–XIV, are possible with respect to the location and configuration of the double bond in the nitrile group containing side chain:

It will be further apparent that the compounds of the invention can exist in various stereoisomeric and enantiomorphic forms with respect to the substituents on the six-membered ring depending on their orientation relative to the plane of the ring. This can be illustrated by the reaction product of the cyanoacetic ester synthesis using 2-formyl-p-menthane from d,l-p-1-menthene. As stated above there is a possibility of a mixture of eight 2-formyl-p-menthanes, III–X, derived from a d,l-mixture of p-1-menthenes. Such a mixture, reacted with cyanoacetic acid followed by decarboxylation, yields a mixture which can contain twelve isomeric nitriles and twelve enantiomorphs thereof. The resulting 24 possible compounds are as follows:

(E)-3-((1R, 2R, 4R)-1-methyl-4-isopropylcyclohexyl-2)acrylonitrile (E)-3-((1S, 2R, 4R)-1-methyl-4-isopropylcyclohexyl-2)acrylonitrile (E)-3-((1R, 2S, 4R)-1-methyl-4-isopropylcyclohexyl-2)acrylonitrile (E)-3-((1R, 2R, 4S)-1-methyl-4-isopropylcyclohexyl-2)acrylonitrile (E)-3-((1S, 2S, 4S)-1-methyl-4-isopropylcyclohexyl-2)acrylonitrile (E)-3-((1R, 2S, 4S)-1-methyl-4-isopropylcyclohexyl-2)acrylonitrile (E)-3-((1S, 2R, 4S)-1-methyl-4-isopropylcyclohexyl-2)acrylonitrile (E)-3-((1S, 2S, 4R)-1-methyl-4-isopropylcyclohexyl-2)acrylonitrile (Z)-3-((1R, 2R, 4R)-1-methyl-4-isopropylcyclohexyl-2)acrylonitrile (Z)-3-((1S, 2R, 4R)-1-methyl-4-isopropylcyclohexyl-2)acrylonitrile (Z)-3-((1R, 2S, 4R)-1-methyl-4-isopropylcyclohexyl-2)acrylonitrile (Z)-3-((1R, 2R, 4S)-1-methyl-4-isopropylcyclohexyl-2)acrylonitrile (Z)-3-((1S, 2S, 4S)-1-methyl-4-isopropylcyclohexyl-2)acrylonitrile (Z)-3-((1R, 2S, 4S)-1-methyl-4-isopropylcyclohexyl-2)acrylonitrile (Z)-3-((1S, 2R, 4S)-1-methyl-4-isopropylcyclohexyl-2)acrylonitrile (Z)-3-((1S, 2S, 4R)-1-methyl-4-isopropylcyclohexyl-2)acrylonitrile (E)-3-((1R, 4R)-1-methyl-4-isopropylcyclohexylidene-2)propanenitrile (E)-3-((1R, 4S)-1-methyl-4-isopropylcyclohexylidene-2)propanenitrile
(E)-3-((1S, 4R)-1-methyl-4-isopropylcyclohexylidene-2)propanenitrile
(E)-3-((1S, 4S)-1-methyl-4-isopropylcyclohexylidene-2)propanenitrile
(Z)-3-((1R, 4R)-1-methyl-4-isopropylcyclohexylidene-2)propanenitrile
(Z)-3-((1R, 4S)-1-methyl-4-isopropylcyclohexylidene-2)propanenitrile
(Z)-3-((1S, 4R)-1-methyl-4-isopropylcyclohexylidene-2)propanenitrile
(Z)-3-((1S, 4S)-1-methyl-4-isopropylcyclohexylidene-2)propanenitrile.

The ratio of nitrile isomers formed can be influenced by the reaction conditions employed and by the choice of starting material with respect to the optical configuration. According to the invention it was found that in the above mentioned Wittig-type reactions of the oxo-compounds with cyanoalkyl phosphonates predominantly the isomers with α,β-unsaturated nitrile side chains are formed. The E/Z ratio of the double bond in the nitrile group containing side chain can be influenced to a certain extent by the solvent-base combination employed in this reaction. Aprotic conditions favor a higher content of Z-isomers than do protic conditions. The formation of β,γ-unsaturated nitrile-isomers occurs to a considerable extent in the decarboxylation of the alkylidene cyanoacetic acids prepared from cyanoacetic acid or esters and the oxo-compounds.

As the examples will demonstrate, the nitriles of this invention exhibit a wide variety of odor effects. They can be used alone as fragrances per se or they can be used as components of a fragrance composition. The term "fragrance composition" is used to denote a mixture of compounds including, for example, natural oils, synthetic oils, alcohols, aldehydes, ketones, esters, lactones, ethers, hydrocarbons and other classes of chemical compounds which are admixed so that the combined odors of the individual components produce a pleasant or desired fragrance. Such fragrance compositions or the novel compounds of this invention can be used in conjunction with carriers, vehicles or solvents containing also, as needed, dispersants, emulsifiers, surface-active agents, aerosol propellants and the like.

In fragrance compositions the individual components contribute their particular olfactory characteristics, but the overall effect of the composition is the sum of the effect of each ingredient. Thus, the nitriles of this invention can be used to alter, enhance, or reinforce the aroma characteristics of the other natural or synthetic materials making up the fragrance composition, for example, by highlighting or moderating the olfactory reaction contributed by another ingredient or combination of ingredients.

The amount of nitrile which will be effective depends on many factors including the other ingredients, their amounts and the effects which are desired. It has been found that as little as 0.01% by weight of compounds of this invention can be used to alter the effect of a fragrance composition. The amount employed will depend on considerations of cost, nature of end product, the effect desired in the finished product, and the particular fragrance sought, but normally will not be more than about 30% by weight.

The compound disclosed herein can be used in a wide variety of applications such as, e.g., detergents and soaps; space deodorants perfumes, colognes; after-shave lotions; bath preparations such as bath oil and bath salts; hair preparations such as lacquers; brilliantines, pomades and shampoos; cosmetic preparations such as creams, deodorants, hand lotions, and sun screens; powders such as talcs, dusting powders, face powder; as masking agents, e.g., in household products such as bleaches, and in technical products such as shoe polish and automobile wax.

The following examples illustrate the invention, which is not to be considered restricted thereto but is limited solely as indicated in the appended claims.

EXAMPLE 1

A mixture of 15 g (0.089 mole) 2-formyl-p-menthane, obtained from (+)-p-1-menthene, $(\alpha)_D^{20} = +86.8°$; via a Prins reaction with paraformaldehyde (as described in Bull. Soc. Chim. France 1960; 98) followed by hydrogenation and oxidation, 8 g cyanoacetic acid (0.094 mole), 1 g ammonium acetate, 50 ml N,N-dimethylformamide and 50 ml toluene was refluxed with azeotropic removal of the water formed. After the theoretical amount of water was collected the toluene was distilled off and the residue was refluxed for 2¼ hr. The cooled reaction mixture was poured into water and extracted twice with ether. The ether layers were washed with saturated $KHCO_3$ solution, then with saturated NaCl solution and finally dried with $Na_2SO_4$. After evaporation of the ether, distillation of the residue yielded 14.5 g (0.076 mole = 85%) isomeric mixture of 3-(1-methyl-4-isopropylcyclohexyl-2)acrylonitrile and 3-(1-methyl-4-isopropylcyclohexylidene-2)propanenitrile, b.p. 92°–98° C. at 0.7 mm Hg, $n_D^{20} = 1.4805$, with green, petit grain like, leathery, woody odour.

EXAMPLE 2

The procedure of Example 1 was repeated starting with 2-formyl-p-menthane prepared from (−)-p-1-menthene, $(\alpha)_D^{20} = -80.6°$, via the Prins reaction with paraformaldehyde. Obtained was 83% yield of the isomeric mixture of 3-(1-methyl-4-isopropylcyclohexyl-2)acrylonitrile and 3-(1-methyl-4-isopropylcyclohexylidene-2)propanenitrile, b.p. 77°–82° C. at 0.3 mm Hg, $n_D^{20} = 1.4792$, with an odour similar to that of the nitrile mixture of Example 1.

EXAMPLE 3

To a suspension of 1.8 g 80% sodium hydride (0.060 mole) in 40 ml N,N-dimethylformamide was added dropwise in the course of 20 minutes a mixture of 10.5 g (0.060 mole) diethyl cyanomethylphosphonate and 10 ml N,N-dimethylformamide. The reaction temperature was maintained at 30° C. during the addition and for an additional ¾ hour. Then 10 g (0.060 mole) 2-formyl-p-menthane used in Example 1 was added dropwise in 30 minutes and the reaction mixture was kept at 40° C. for two hours, cooled and 10 ml acetic acid and 75 ml water were added respectively. The organic material was taken up in ether and washed with saturated $KHCO_3$ solution, and with saturated NaCl solution and dried with $Na_2SO_4$. After evaporation of the solvent, distillation yielded 9.5 g (0.050 mole = 83%) 3-(1-methyl-4-isopropylcyclohexyl-2)acrylonitrile, b.p. 87°–89° C. at 0.6 mm Hg, $n_D^{20} = 1.4802$, with green, watery, fatty odour.

EXAMPLE 4

Analogously to Example 3 was prepared 2-n-butyl-3-(1-methyl-4-isopropylcyclohexyl-2)acrylonitrile from 2-formyl-p-menthane used in Example 1 and diethyl 1-cyanopentylphosphonate in 66% yield, with woody odour, b.p. 109°-114° C. at 0.3 mm Hg, $n_D^{20}=1.4749$.

EXAMPLE 5

Analogously to Example 1 was prepared ethyl 2-cyano-3-(1-methyl-4-isopropylcyclohexyl-2)acrylate from 2-formyl-p-menthane used in Example 1 and ethyl cyanoacetate in 73% yield, b.p. 110°-113° C. at 0.2 mm Hg, $n_D^{20}=1.4828$.

EXAMPLE 6

To a suspension of 2.6 g 80% sodium hydride (0.090 mole) in 50 ml N,N-dimethylformamide was added dropwise in five minutes 15 g (0.057 mole) ethyl 2-cyano-3-(1-methyl-4-isopropylcyclohexyl-2)acrylate prepared in Example 5. The reaction temperature was kept at 40° C. for four hours. Then 18.8 g (0.114 mole) 1-bromohexane was added in 15 minutes at 40° C. and the mixture was stirred at 40° C. for 44 hours, cooled to roomtemperature, acidified with 10 ml acetic acid, diluted with 75 ml water and extracted with ether. The ether extracts were washed with saturated $KHCO_3$ solution and saturated NaCl solution, then dried with $Na_2SO_4$. After evaporation of the solvent 23 g residue was obtained, which was taken up in 10 ml absolute ethanol and treated with a solution of 3,5 g potassium hydroxide in 15 ml absolute ethanol for 5 minutes at 35° C. After evaporation of the ethanol by means of a rotatory evaporator the residue was taken up in water, acidified with dilute HCl solution and extracted with ether. After evaporation of the solvent the crude cyanoacid was refluxed in 25 ml N,N-dimethylformamide for 2 hours. Distillation yielded 10 g (0.364 mole=64%) 2-n-hexyl-3-(1-methyl-4-isopropylcyclohexylidene-2)propanenitrile with green fatty odour, b.p. 119°-121° C. at 0.2 mm Hg, $n_D^{20}=1.4735$.

EXAMPLE 7

To a mixture of 10 g (0.060 mole) 2-formyl-p-menthane used in Example 1, 6.8 g (0.060 mole) ethyl cyanoacetate, 0.35 g acetic acid and 40 ml dioxane was added, at 20° C., 0.5 ml piperidine. After stirring for an additional 10 minutes at roomtemperature 0.5 g palladium on charcoal was added and the mixture was hydrogenated at roomtemperature and atmospheric pressure untill the theoretical amount of hydrogen was taken up. The catalyst was removed by filtration and after evaporation of the solvent the mixture was taken up in ether, washed with water, dilute hydrochloric acid, saturated $KHCO_3$ solution and saturated NaCl solution respectively and dried with $Na_2SO_4$. Distillation yielded 12 g (0.045 mole=75%) ethyl 2-cyano-3-(1-methyl-4-isopropylcyclohexyl-2)propionate, b.p. 121°-127° C. at 0.4 mm Hg, which was saponified and decarboxylated analogous to the procedure of Example 6. Obtained was 69% 3-(1-methyl-4-isopropylcyclohexyl-2)propanenitrile with fruity green woody odour, b.p. 87°-89° C. at 0.4 mm Hg, $n_D^{20}=1.4670$.

EXAMPLE 8

Analogously to Example 2 was prepared 3-(1-methyl-4-isopropylcyclohexenyl-6)-2-butenenitrile from 6-acetyl-p-1-menthene, prepared by acetylation of (+)-p-1-menthene as described in Brit. Pat. No. 870.001. $(\alpha)_D^{20}=+86.8°$, and diethyl cyanomethylphosphonate, in 68% yield with woody cuminic odour. B.p. 80°-83° C. at 0.5 mm Hg, $n_D^{20}=1.4991$.

EXAMPLE 9

Analogously to Example 2 was prepared 2-methyl-3-(1-methyl-4-isopropylcyclohexenyl-6)-2-butenenitrile from 6-acetyl-p-1-menthene, obtained by acetylation of (−)-p-1-menthene, $(\alpha)_D^{20}=-80.6°$, and diethyl 1-cyanoethylphosphonate in 44% yield with cuminic greenish floral odour, b.p. 88°-92° C. at 0.3 mm Hg, $n_D^{20}=1.4948$.

EXAMPLE 10

Analogously to Example 2 was prepared 3-(1-methyl-4-isopropylcyclohexenyl-2)-2-butenenitrile from 2-acetyl-p-1-menthene, prepared by alkaline isomerization (cf. Ber. 100, 1892 (1967) for 2-acetyl-3-carene) of the 6-acetyl-p-1-menthene used in Example 8 and diethyl cyanomethylphosphonate in 68% yield with woody cinnamic odour. B.p. 96°-101° C. at 0.4 mm Hg, $n_D^{20}=1.4981$.

EXAMPLE 11

Analogously to Example 1 was prepared an isomeric mixture of 3-(3-methyl-6-isopropenylcyclohexenyl-4)acrylonitrile and 3-(3-methyl-6-isopropenylcyclohexenylidene-4)propanenitrile from 2-methyl-5-isopropenyl-3-cyclohexenecarbaldehyde (Ber. 93, 2673 (1960)) and cyanoacetic acid in 67% yield with greenish leathery woody odour, b.p. 78°-84° C. at 0.3 mm Hg, $n_D^{20}=1.5040$.

EXAMPLE 12

Analogously to Example 1 was prepared an isomeric mixture of 3-(1-methyl-4-isopropenylcyclohexenyl-6)acrylonitrile and 3-(1-methyl-4-isopropenylcyclohexenylidene-6)propanenitrile from 2-methyl-5-isopropenyl-2-cyclohexenecarbaldehyde (Bull.Acad.Polon.Ser.-Sci.Chim. 13, 751 (1968) and cyanoacetic acid in 27% yield with basilicum, fennel like odour, b.p. 86°-90° C. at 0.2 mm Hg, $n_D^{20}=1.5294$.

EXAMPLE 13

A perfume composition is prepared by admixing the following ingredients:

| | |
|---|---|
| 200 | bergamot oil |
| 100 | lemon oil |
| 60 | Vertofix (IFF) |
| 50 | lavender oil |
| 50 | alpha-hexylcinnamic aldehyde |
| 50 | hydroxycitronellal |
| 50 | benzyl acetate |
| 50 | gamma-methylionone |
| 40 | patchouli oil |
| 40 | geranyl acetate |
| 40 | phenylethyl alcohol |
| 30 | amyl salicilate |
| 30 | musk-ambrette |
| 30 | sandalwood oil |
| 20 | cinnamic alcohol |
| 20 | ylang-ylang oil I |
| 20 | geranium oil, Bourbon |
| 20 | cinnamon oil |
| 20 | oakmoss absolute decolorised |
| 15 | Celestolide (IFF) |
| 10 | cumarine |
| 10 | dihydromyrcenol |
| 10 | isoeugenyl acetate |
| 10 | undecylenic aldehyde - 10%-sol. |
| 5 | styrallyl acetate |
| 5 | Aurantiol (Schiff's base hydroxycitronellal-methyl anthranilate) |
| 5 | cyclamenaldehyde |

| 10 | isomeric nitrile mixture of Example 12 |
|---|---|
| 1000 | |

The addition of 10% of the nitrile mixture of Example 12 gives a clear and desirable effect.

EXAMPLE 14

A perfume composition is prepared by admixing the following ingredients:

| 160 | linalol |
|---|---|
| 100 | cedarwood oil |
| 100 | gamma-methylionone |
| 70 | geraniol |
| 70 | citronellol |
| 60 | alpha-amylcinnamic aldehyde |
| 50 | benzyl acetate |
| 50 | Vertenex (IFF) |
| 50 | amyl salicilate |
| 40 | phenylethyl alcohol |
| 40 | Lyral (IFF) |
| 30 | Celestolide (IFF) |
| 30 | musk-ambrette |
| 20 | cananga oil |
| 20 | Lilial (Givaudan) |
| 20 | oakmoss absolute |
| 15 | Dimethylbenzylcarbinyl acetate |
| 15 | dihydromyrcenol |
| 10 | litsea cubeba-oil |
| 10 | cinnamon leaf oil |
| 5 | Aurantiol (Schiff's base hydroxycitronellal-methyl anthranilate) |
| 5 | laurylaldehyde |
| 5 | methylnonylacetaldehyde |
| 5 | anisic alcohol |
| 15 | isomeric nitrile mixture of Example 1 |
| 1000 | |

The addition of 1,5% of the nitrile mixture of Example 1 gives a clear and desirable effect.

What I claim and desire to protect by Letters Patent is:

1. A compound having the formula:

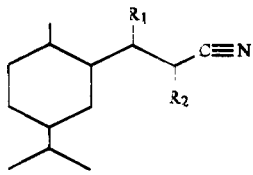

wherein $R_1$ is hydrogen and $R_2$ is hydrogen or an alkyl group of 1 to 6 carbon atoms.

* * * * *